United States Patent
Nöcker et al.

(10) Patent No.: US 12,121,605 B2
(45) Date of Patent: Oct. 22, 2024

(54) DYEING COMPOSITION FOR KERATIN FIBERS COMPRISING A DIRECT DYE AND AN ORGANIC ALKALIZING AGENT, METHOD FOR DYEING; AND KIT-OF-PARTS THEREOF

(71) Applicant: KAO CORPORATION, Tokyo (JP)

(72) Inventors: Bernd Nöcker, Darmstadt (DE); Steven Breakspear, Darmstadt (DE); Fariba Ghiasi, Darmstadt (DE); Anna Neu, Darmstadt (DE); Masahiko Watanabe, Tokyo (JP); Fumina Abo, Tokyo (JP)

(73) Assignee: KAO CORPORATION, Tokyo (JP)

( * ) Notice: Subject to any disclaimer, the term of this patent is extended or adjusted under 35 U.S.C. 154(b) by 21 days.

(21) Appl. No.: 18/245,766

(22) PCT Filed: Sep. 20, 2021

(86) PCT No.: PCT/EP2021/075791
§ 371 (c)(1),
(2) Date: Mar. 17, 2023

(87) PCT Pub. No.: WO2022/069280
PCT Pub. Date: Apr. 7, 2022

(65) Prior Publication Data
US 2023/0390173 A1 Dec. 7, 2023

(30) Foreign Application Priority Data
Sep. 30, 2020 (EP) .................................... 20199262

(51) Int. Cl.
*A61Q 5/10* (2006.01)
*A61K 8/22* (2006.01)
*A61K 8/41* (2006.01)
*A61Q 5/06* (2006.01)

(52) U.S. Cl.
CPC ................. *A61K 8/41* (2013.01); *A61K 8/22* (2013.01); *A61Q 5/065* (2013.01); *A61K 2800/4322* (2013.01)

(58) Field of Classification Search
CPC .... A61K 8/41; A61K 8/22; A61K 2800/4322; A61K 8/49; A61Q 5/065

USPC ............................................................ 8/405
See application file for complete search history.

(56) References Cited

U.S. PATENT DOCUMENTS

| 2017/0105921 | A1* | 4/2017 | Fabbi | A61K 8/41 |
| 2017/0196791 | A1 | 7/2017 | Nojiri | |
| 2017/0216174 | A1* | 8/2017 | Aeby | A61Q 5/08 |
| 2017/0258695 | A1* | 9/2017 | Consoli | A61K 8/55 |
| 2017/0354581 | A1* | 12/2017 | Consoli | A61Q 5/10 |
| 2020/0289389 | A1 | 9/2020 | Monda et al. | |

FOREIGN PATENT DOCUMENTS

| EP | 1 366 752 A1 | 12/2003 | |
| EP | 2 979 683 A1 | 2/2016 | |
| EP | 3156041 A1 * | 4/2017 | A61Q 5/10 |
| JP | 2016-108296 A | 6/2016 | |
| JP | 2017-522351 A | 8/2017 | |
| JP | 2019-151615 A | 9/2019 | |
| WO | WO 2015/186817 A1 | 12/2015 | |
| WO | WO 2019057829 A1 * | 3/2019 | A61Q 5/10 |

OTHER PUBLICATIONS

International Search Report issued Feb. 7, 2022, in PCT/EP2021/075791, filed on Sep. 20, 2021, 3 pages.
Written Opinion issued Feb. 7, 2022, in PCT/EP2021/075791, filed on Sep. 20, 2021, 5 pages.
European Search Report issued Mar. 17, 2021, in European Patent Application No. 20199262.5 filed Sep. 30, 2020, 6 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A dyeing composition for keratin fibers, including one or more direct dyes selected from HC Blue 18, HC Red 18, HC Yellow 16, and salts thereof, and tris-(hydroxymethyl)-aminomethane and salts thereof. A method for dyeing keratin fibers, including mixing the composition with a second aqueous composition having a pH in a range of 1 to 6 and optionally including one or more oxidizing agents to yield a ready-to-use composition having a pH in a range of 7 to 12, applying the ready-to-use composition onto the keratin fibers and leaving it for a time period in a range of 1 min to 60 min, and rinsing-off the keratin fibers and optionally shampooing the keratin fibers.

18 Claims, No Drawings

DYEING COMPOSITION FOR KERATIN FIBERS COMPRISING A DIRECT DYE AND AN ORGANIC ALKALIZING AGENT, METHOD FOR DYEING; AND KIT-OF-PARTS THEREOF

CROSS REFERENCE TO RELATED APPLICATIONS

This application is a National Stage entry under 35 U.S.C. § 371 of PCT/EP2021/075791, filed on Sep. 20, 2021, and claims priority to European Patent Application No. 20199262.5, filed on Sep. 30, 2020. The entire contents of both are incorporated herein by reference.

FIELD OF THE INVENTION

The present invention is directed to a dyeing composition for keratin fibers comprising certain direct dyes and a particular alkalizing agent, and method for dyeing.

BACKGROUND OF THE INVENTION

Direct dyes have been of particular interest of cosmetic industry over the past decade. In contrast to their oxidative counterparts, direct dyes are easier to apply to keratin fibers, but often lack durability on keratin fibers. In addition, on grey hair direct dyes often lack dyeing intensity without the use of oxidative dyes.

Applicant has developed new direct dyes (EP1366752), which complement the availability and color range of the existing ones. A series of the aforementioned developed dyes comprises HC Blue 18, HC Red 18, and HC Yellow 16.

EP2979683 discloses tris-(hydroxymethyl)-aminomethane as alkalizing agent for oxidative dyeing compositions and generally discloses the combination with direct dyes. Improved evenness of coloration with oxidative dyes has been found.

However, the prior art has not satisfactorily solved the dyeing intensity and durability challenge of direct dyes, and, therefore, there is a real need to develop direct dyeing compositions for keratin fibers, which have improved dyeing intensity and durability, in particular on hair with prior hair damage.

SUMMARY OF THE INVENTION

Therefore, the first object of the present invention is a dyeing composition for keratin fibers, preferably for human keratin fibers, more preferably for human hair, comprising:
  a) one or more direct dye(s) selected from HC Blue 18, HC Red 18, HC Yellow 16, and/or their salt(s), and/or their mixture(s), and
  b) tris-(hydroxymethyl)-aminomethane and/or its salt(s).

The second object of the present invention is a two-part dyeing composition characterized in that the first part is the composition as defined above, and the second composition is an aqueous composition having a pH in the range of 1 to 6 and optionally comprising one or more oxidizing agent(s).

The third object of the present invention is a kit-of-parts comprising
  a first dyeing composition comprising HC Blue 18, HC Red 18, HC Yellow 16, and/or their salt(s), and/or their mixtures as compound(s) according to group a) and one or more compound(s) according to group b),
  a second composition having comprising one or more direct dye(s) selected from HC Yellow 1 and/or Disperse black 9, and/or their salt(s), and/or their mixtures, and
  optionally a third aqueous composition having a pH in the range of 1 to 6 and optionally comprising one or more oxidizing agent(s).

The fourth object of the present invention is a method for dyeing of keratin fibers preferably human keratin fibers, more preferably human hair, comprising the steps of:
  i) applying the composition as defined above onto keratin fibers and leaving it for a time period in the range of 1 min to 60 min,
  ii) optionally rinsing it off and optionally drying the keratin fibers.

The fifth object of the present invention is a method for dyeing keratin fibers, preferably human keratin fibers, more preferably human hair, comprising the steps of:
  iii) mixing the composition as defined above with a second aqueous composition having a pH in the range of 1 to 6 and optionally comprising one or more oxidizing agent(s), preferably hydrogen peroxide, to yield a ready-to-use composition having a pH in the range of 7 to 12,
  iv) applying the ready-to-use composition onto keratin fibers and leaving it for a time period in the range of 1 min to 60 min,
  v) rinsing-off the keratin fibers and optionally shampooing the keratin fibers.

DETAILED DESCRIPTION OF THE INVENTION

Inventors of the present invention have surprisingly found out that dyeing intensity, durability, and wash fastness of certain direct dyes is improved in the presence of tris-(hydroxymethyl)-aminomethane and/or its salt(s) as alkalizing agent. Moreover, such an inventive dyeing composition improves cosmetic properties of keratin fibers such as feel, shine, and touch.

Dyeing Composition

The present invention is directed to a dyeing composition for keratin fibers, preferably for human keratin fibers, more preferably for human hair, comprising:
  a) one or more direct dye(s) selected from HC Blue 18, HC Red 18, HC Yellow 16, and/or their salt(s), and/or their mixture(s), and
  b) tris-(hydroxymethyl)-aminomethane and/or its salt(s).

It is preferred from the viewpoint of dyeing intensity that the total concentration of compound(s) according to group a) is 0.001% by weight or more, more preferably by weight or more, further more preferably 0.05% by weight or more, still further more preferably 0.1% by weight or more, calculated to the total weight of the composition.

It is preferred from the viewpoint of economic reasons and cosmetic safety that the total concentration of compound(s) according to group a) is 10% by weight or less, more preferably 0.5%% by weight or less, further more preferably 2% by weight or less, still further more preferably 1% by weight or less, calculated to the total weight of the composition.

For attaining the above-mentioned effects, it is preferred that the total concentration of compound(s) according to group a) is in the range of 0.001% to 10% by weight, preferably in the range of 0.002% to 5% by weight, more preferably in the range of to 2% by weight, still further more preferably 0.1% to 1% by weight, calculated to the total weight of the composition.

It is preferred from the viewpoint of dyeing intensity that the total concentration of compound(s) according to group b) is 0.1% by weight or more, more preferably by weight or more, further more preferably 0.5% by weight or more, still further more preferably 0.75% by weight or more, still further more preferably 1% by weight or more, calculated to the total weight of the composition.

It is preferred from the viewpoint of economic reasons and cosmetic safety that the total concentration of compound (s) according to group b) is 40% by weight or less, more preferably 30%% by weight or less, further more preferably 20% by weight or less, still further more preferably 15% by weight or less, still further more preferably 12.5% by weight or less, calculated to the total weight of the composition.

For attaining the above-mentioned effects, it is preferred that the total concentration of compound(s) according to group b) is in the range of 0.1% to 40% by weight, preferably in the range of 0.25% to 30% by weight, more preferably in the range of 0.5% to 20% by weight, more preferably in the range of 0.75% to 15% by weight, still further more preferably in the range of 1% to 12.5% by weight, calculated to the total weight of the composition.

It is further preferred from the viewpoint of viewpoint of dyeing intensity, that the weight ratio of compound(s) according to group b) to compound(s) according to group a) is 0.1 or more, more preferably 0.5 or more, further more preferably 1 or more, still further more preferably 1.5 or more, still more preferably 5 or more, further still more preferably 10 or more.

It is further preferred from the viewpoint of viewpoint of dyeing intensity, formulation stability, and cosmetic safety that the weight ratio of compound(s) according to group b) to compound(s) according to group a) is 200 or less, more preferably 180 or less, further more preferably 150 or less, still further more preferably 125 or less, still further more preferably 100 or less, still more preferably 50 or less.

For attaining the above-mentioned effects, it is preferred that the weight ratio of compound(s) according to group b) to compound(s) according to group a) is in the range of 0.1 to 200, preferably in the range of 0.5 to 180, more preferably in the range of 1 to 150, further more preferably in the range of 1.5 to 125, still more preferably in the range of 5 to 100, still more preferably in the range of 10 to 50.

Cosmetic Forms of Composition—Aqueous Composition

In one aspect of the present invention, the composition is an aqueous composition.

The term 'aqueous' denotes a composition that comprises a majority of water, i.e., the composition preferably comprises water at 50% by weight or more, further more preferably at 60% by weight or more, still more preferably at 70% by weight or more, still further more preferably at 80% by weight or more, calculated to the total weight of the composition, from the viewpoint of achieving a cosmetically acceptable composition.

It is further preferred from the viewpoint of dyeing intensity that the composition comprises water at 98% by weight or less, more preferably at 95% by weight or less, further more preferably at 92% by weight or less, calculated to the total weight of the composition.

For achieving the above-mentioned effects, it is preferred that the total concentration of water is in the range of 50% to 98% by weight, more preferably in the range of 60% to 95% by weight, further more preferably in the range of 70% to 92% by weight, still more preferably in the range of 80% to 92% by weight, calculated to the total weight of the composition.

It is preferred from the viewpoint of dyeing performance that the pH of the aqueous composition is 7 or more, more preferably the pH is 7.5 or more, further more preferably the pH is 8 or more, still further more preferably the pH is 8.5 or more.

It is preferred from the viewpoint of hair damage and dyeing performance that the pH of the composition is 12 or less, more preferably the pH is 11 or less, still more preferably the pH is 10.5 or less.

For attaining the above mentioned effects, it is preferred that the aqueous composition has a pH in the range of 7 to 12, preferably in the range of 7.5 to 11, more preferably in the range of 8 to 10.5, further more preferably in the range of 8.5 to 10.5.

In one aspect of the present invention, the aqueous composition may comprise one or more organic solvent(s) as explained below as compound(s) according to group c). For this aspect, suitable concentrations of compound(s) according to group c) are in the range of 0.1% to 10% by weight, calculated to the total weight of the composition Liquid Composition Comprising Less than 1% by Weight of Water In another aspect of the present invention, the composition is a liquid composition at and atmospheric pressure comprising one or more organic solvent(s) as compound(s) according to group c) and less than 1% by weight of water, calculated to the total weight of the composition. Preferably, the composition is anhydrous, from the viewpoint of dye stability.

The term 'liquid' denotes a physical state at 25° C. and atmospheric pressure, i.e., the dyeing composition is liquid at room temperature.

The term 'anhydrous' denotes a composition, which is free of added water. This does not exclude the presence of residual moisture from air or crystal water bound to ingredients.

For this aspect of the present invention, the composition may comprise one or more organic solvent(s) as compound (s) according to group c).

The organic solvent(s) may be selected to dissolve the compounds according to groups a) to b). Preferred solvents are mono-, di-, and trivalent alcohols and/or their mixtures.

Preferred mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

It is further preferred from the viewpoint of solution stability that the total concentration of compound(s) according to group c) is 75% by weight or more, more preferably 80% by weight or more, further more preferably 85% by weight or more, calculated to the total weight of the composition.

It is further preferred from the viewpoint of dyeing intensity that the total concentration of compound(s) according to group c) is 98% by weight or less, more preferably 95% by weight or less, further more preferably 92% by weight or less, calculated to the total weight of the composition.

For attaining the above-mentioned effects, it is preferred that the total concentration of compound(s) according to group c) is in the range of 75% to 98% by weight, more preferably 80% to 95% by weight, further more preferably in the range of 85% to 92% by weight, calculated to the total weight of the composition.

Powder Composition

In one aspect of the present invention, the composition may be a dyeing powder composition.

The term 'powder' denotes a solid composition at 25° C. and atmospheric pressure. The term relates to freely flowing powders as well as compressed powders such as tablets. The powder composition may also comprise water as long as its nature of the solid state at 25° C. is unchanged. Depending on the type of powder, a water content of 10% by weight or more, calculated to the total weight of the composition, may be acceptable.

It is preferred from the viewpoint of composition stability and convenience of use that the composition comprises one or more pulverulent excipient as compound(s) according to group d).

The term 'excipient' denotes a compound, which may act as filling material and dispersant for the other compounds of the dyeing composition and do not react with the dyes and the alkalizing agent, and, thus, confer the powder a high degree of storage stability over an extended period of time.

The dyeing powder composition of the present invention may comprise an organic and/or an inorganic pulverulent excipient in which the alkalizing agent and direct dyes are dispersed.

Suitable organic and/or an inorganic pulverulent excipients are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total of the composition, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total of the composition, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of the composition.

Lipophilic Compounds According to Group e)

It is preferred from the viewpoint of further increasing dyeing intensity that the composition of the present invention comprises one or more lipophilic compound(s) being liquid at 25° C. under atmospheric pressure as compound(s) according to group e).

Suitable compounds according to group e) are natural and/or vegetable oils, petrolatum-based compounds, linear or branched, saturated or unsaturated fatty alcohols with C12 to C22, and fatty acid esters consisting of linear or branched, saturated or unsaturated fatty acids with C12 to C22 being esterified with linear or branched primary alcohols with C3 to C12, and silicones.

Suitable natural and/or vegetable oils are olive oil, almond oil, avocado oil, wheatgerm oil, and castor oil.

Suitable petrolatum-based compounds are liquid paraffins, especially paraffinum perliquidum and paraffinum subliquidum, and mineral oil, in particular white mineral oil.

Suitable comprises fatty compounds selected from linear or branched, saturated or unsaturated fatty alcohols with C12 to C22 are lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, behenyl alcohol, and/or their mixtures, such as cetearyl alcohol.

Suitable examples for fatty acid esters consisting of linear or branched, saturated or unsaturated fatty acids with C12 to C22 being esterified with linear or branched primary alcohols with C3 to C18 are octyl palmitate, isocetyl palmitate, isopropyl palmitate, octyl stearate, oleyl oleate, and myristyl myristate, as well as their mixtures.

Suitably, the compositions may also comprise lipophilic ingredients such as silicones for example linear polysiloxanes such as dimethicones with various consistency and dimethiconols, aminated silicones with primary, secondary, tertiary or quaternary ammonium groups such as amodimethicone, polysilicone 9, and quaternium 80, cyclic silicones such as cyclomethicones, arylated silicones such as phenyl trimethicone; C10- to C36-fatty acid triglycerides, as well as their mixtures.

In case the composition of the present invention is an aqueous composition as disclosed above, it is preferred from the viewpoint of further increasing dyeing intensity that it is an emulsion and comprises one or more compound(s) according to group e) selected from fatty alcohols having an branched or linear, saturated or unsaturated carbon chain length in the range of C12 to C22, fatty acids having an branched or linear, saturated or unsaturated carbon chain length in the range of C12 to C22, ester oils, vegetable oils, silicone oil, paraffin oils.

Suitable concentrations of compound(s) according to e) in emulsions range from 0.5% to 20% by weight, preferably from 1% to 10% by weight, calculated to the total weight of the composition.

In case the composition of above is a powder composition, the lipophilic compounds recited above confer the powder dust-free properties. Suitable concentrations of compound(s) according to e) are in the range of 0.5% to 10% by weight, calculated to the total weight of the composition.

In one aspect of the present invention, the powder composition may also comprise one or more one or more organic solvent(s) as compound(s) according to group c), as explained above. Suitable concentrations of compound(s) according to c) are in this case in the range of 0.1% to 5% by weight, calculated to the total weight of the composition.

Surfactants

It is further preferred from the viewpoint of composition stability and mixability as well as wetting of keratin fibers that the composition of the present invention further comprises one or more surfactant(s) as compound(s) according to f), more preferably selected from non-ionic, cationic, anionic, zwitterionic/amphoteric surfactant(s).

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-

$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolam ides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolam ides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "PluronicsR", as well as fatty alcohol ethoxylates, $C_{10}$-$C_{22}$-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable am photeric/zwitterionic surfactants are in particular the various known betaines such as alkyl betaines, fatty acid am idoalkyl betaines and sulfobetaines, for example, lauryl hydroxysulfobetaine; long-chain alkyl amino acids, such as cocoaminoacetate, cocoaminopropionate and sodium cocoamphopropionate and -acetate are also suitable.

Typical cationic surfactants are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

It is preferred from the viewpoint of composition stability, wetting of keratin fibers, and ingredient dispersability that the total concentration of compound(s) according to f) is by weight or more, preferably 0.2% by weight or more, further more preferably by weight or more, calculated to the total weight of the composition.

It is preferred from the viewpoint of composition stability, wetting of keratin fibers, and ingredient dispersability that the total concentration of compound(s) according to f) is 5% by weight or less, preferably 4% by weight or less, further more preferably 2.5% by weight or less, calculated to the total weight of the composition.

For attaining the above-mentioned effects, it is preferred that the total concentration of compound(s) according to f) is in the range of 0.1% to 5% by weight, more preferably 0.2% to 4% by weight, further more preferably 0.2% to 2.5% by weight, calculated to the total weight of the composition.

Alkalizing Agent(s) Different from Group b)

It is preferred from the viewpoint of high pH dyeing that the composition of the present invention comprises one or more alkalizing agents different from compound(s) according to group b). More preferably the aforementioned alkalizing agents different from compound(s) according to group b) are selected from ammonia and/or its salt(s), organic alkyl and/or alkanolamines and/or their salt(s), and/or their mixture(s).

Suitable organic alkyl and/or alkanolamines and/or their salt(s) are according to the following general structure:

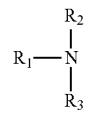

wherein R1, R2, and R3 are independently selected from H, linear C1-C6 alkyl which may be substituted with one hydroxyl group, or branched C3-C12 alkyl or alkanol, wherein at least one of R1, R2, or R3 is different from H, and/or their salts, and/or their mixtures.

Suitably, one or more alkyl and/or alkanolamine(s) and/or its/their salt(s), are selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, and/or its/their salt(s), and/or their mixtures, from the viewpoint of providing alkalinity and cosmetic safety as well as their low odor.

The preferred alkalizing agents different from compound (s) according to group b) is/are selected from ammonia, monoethanolamine, 2-amino-2-methylpropanol, and/or its/their salt(s), and/or their mixtures, from the viewpoint of providing alkalinity and cosmetic safety.

It is preferred from the viewpoint of providing alkalinity that the total concentration of alkalizing agents different from compound(s) according to group b) is 0.1% by weight or more, more preferably 0.25% by weight or more, further more preferably 0.4% by weight or more, calculated to the total weight of the composition.

It is preferred from the viewpoint of providing alkalinity, hair damage, and odor that the total concentration of alkalizing agents different from compound(s) according to group b) is 40% by weight or less, more preferably 30% by weight or less, further more preferably 25% by weight or less, calculated to the total weight of the composition.

For attaining the above-mentioned effects, it is preferred that the total concentration of alkalizing agents different from compound(s) according to group b) is in the range of 0.1% to 40% by weight, preferably in the range of 0.25% to 30% by weight, more preferably in the range of 0.4% to 25% by weight, calculated to the total weight of the composition.

Acids Having at Least One Acidic Proton with a pKa Value of 4 or Less

It is preferred from the viewpoint of dyeing intensity, cosmetic safety, and pH adjustment that the composition of the present invention comprises one or more acid(s) having at least one acidic proton with a pKa value of 4 or less.

Suitable acids may be selected from inorganic or organic acids, and/or their mixtures.

Suitable organic acids are lactic acid, citric acid, malic acid, and succinic acid.

Suitable inorganic acids are phosphoric acid and hydrochloric acid.

Preferred acids from the viewpoint of dyeing intensity, cosmetic safety, and pH adjustment having at least one acidic proton with a pKa value of 4 or less are lactic acid, citric acid, and phosphoric acid, and/or their mixtures. The most preferred acids are lactic acid and citric acid, and/or their mixtures.

Suitable concentration ranges for one or more acid(s) having at least one acidic proton with a pKa value of 4 or less are from 0.01% to 2% by weight, preferably from 0.1% to 1% by weight, calculated to the total weight of the composition.

Other Direct Dyes Different from the Ones of Group a)

In one aspect of the present invention, the composition may comprise one or more direct dye(s) different from the ones according to group a).

Suitable direct dyes may be selected from cationic, anionic and/or non-ionic direct dyes.

The most preferred direct dye(s) different from the ones according to group a) are HC Yellow 1 and Disperse Black 9, and/or their salt(s), and/or their mixture(s), from the viewpoint of improving wash fastness of the composition.

The total concentration of one or more direct dyes other than the ones of groups a) in the composition of the present invention, if present, preferably is 0.01% by weight or more, more preferably 0.05% by weight or more, further more preferably 0.1% by weight or more, calculated to the total weight of the composition, from the viewpoint of wash fastness.

The total concentration of one or more direct dyes other than the ones of groups a) and b) in the composition of the present invention, if present, preferably is 10% by weight or less, more preferably 9% by weight or less, further more preferably 7.5% by weight or less, further more preferably 6% by weight or less, even more preferably 4% by weight or less, calculated to the total weight of the composition, from the viewpoint of economic reasons and wash fastness.

For attaining the above mentioned effects, the total concentration of one or more direct dyes other than the ones of groups a) in the composition of the present invention, if present, is in the range of 0.01% to 10% by weight, preferably 0.05% to 9% by weight, more preferably 0.1% to 7.5% by weight, further more preferably 0.1% to 6% by weight, even more preferably 0.1% to 4% by weight, calculated to the total weight of the composition.

Thickening Polymers

It is advantageous from the viewpoint of cosmetic safety that the composition of the present invention further comprises one or more thickening polymer(s).

Preferably, the thickening polymers are selected from polymers resulting in an aqueous solution and/or aqueous dispersion at pH between 8 and 10 having a viscosity of at least 5,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as (C2-C8)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are by weight or more, more preferably 0.25% by weight or more, more preferably 0.5% by weight or more, calculated to the total weight of the composition, from the viewpoint of providing sufficient viscosity to the composition.

Preferably, the total concentration of thickening polymers of the present invention are 15% by weight or less, more preferably 12% by weight or more, further more preferably 10% by weight or less, calculated to the total weight of the composition, from the viewpoint of providing sufficient viscosity to the composition and cost of goods.

For attaining the above-mentioned effects, it is preferred that the total concentration of thickening polymers in the composition of the present invention is in the range of 0.1% to 15% by weight, preferably 0.25% to 12% by weight, more preferably in the range of 0.5% to 10% by weight, calculated to the total weight of the composition.

Two-Part Dyeing Composition

In one aspect of the present invention, the composition may be part of a two-part dyeing composition characterized in that the first part is the dyeing composition as defined above, and the second composition is an aqueous composition having a pH in the range of 1 to 6 and optionally comprising one or more oxidizing agent(s).

The second aqueous composition preferably comprises hydrogen peroxide as an oxidizing agent. Suitable concentrations range from 0.1% to 20% by weight, preferably 0.25% to 15% by weight, and more preferably 0.5% to 12% by weight, calculated to the total weight of the second aqueous composition.

The pH of the second aqueous composition preferably is in the range of 1.5 to 5, more preferably in the range of 2 to 4.5, adjusted by suitable acids and bases.

It is further preferred from the viewpoint of mixability with the first composition that the second aqueous composition comprises one or more lipophilic compound(s) according to e), as laid out above for the dyeing composition. In such a case, the second aqueous composition is an emulsion and preferably also comprises one or more surfactant(s) as compound(s) according to f), as laid out above for the dyeing composition.

First and second compositions in this aspect of the present invention are intended to be mixed directly prior to application onto keratin fibers.

Kit-of-Parts

The present invention is also directed to a kit-of-parts comprising a first dyeing composition comprising HC Blue 18, HC Red 18, HC Yellow 16, and/or their salt(s), and/or their mixtures as compound(s) according to group a) and one or more compound(s) according to group b), a second composition having comprising one or more direct dye(s) selected from HC Yellow 1 and/or Disperse black 9, and/or their salt(s), and/or their mixtures, and optionally a third aqueous composition having a pH in the range of 1 to 6 and optionally comprising one or more oxidizing agent(s).

The first dyeing composition preferably is the composition as disclosed above.

The second composition may be a dyeing composition comprising one or more alkalizing agent(s) and having a pH in the range of 7 to 12.

However, the second composition may also be a cleansing and/or conditioning composition for keratin fibers, preferably comprising one or more surfactant(s) and one or more direct dye(s) selected from HC Yellow 1 and/or Disperse black 9, and/or their salt(s), and/or their mixtures. Suitable concentrations for these dyes are explained above under the section of other direct dyes different from the ones of group a).

The optional third composition may be identical to the second composition as laid out above for the two-part composition.

Method for Dyeing

The present invention is also directed to a method for dyeing of keratin fibers preferably human keratin fibers, more preferably human hair, comprising the steps of:
i) applying the composition as defined above onto keratin fibers and leaving it for a time period in the range of 1 min to 60 min,
ii) optionally rinsing it off and optionally drying the keratin fibers.

It is preferred from the viewpoint of dyeing intensity and dyeing method economy that the leave-on time as defined in step i) is in the range of 2 min to 45 min, more preferably in the range of 5 min to 40 min, further more preferably in the range of 10 min to 30 min.

It is further preferred from the viewpoint of cosmetic safety that the composition is rinsed-off in step ii).

The present invention is also directed to a method for dyeing keratin fibers, preferably human keratin fibers, more preferably human hair, comprising the steps of:
iii) mixing the composition as defined above with a second aqueous composition having a pH in the range of 1 to 6 and optionally comprising one or more oxidizing agent(s), preferably hydrogen peroxide, to yield a ready-to-use composition having a pH in the range of 7 to 12,
iv) applying the ready-to-use composition onto keratin fibers and leaving it for a time period in the range of 1 min to 60 min,
v) rinsing-off the keratin fibers and optionally shampooing the keratin fibers.

It is preferred from the viewpoint of color intensity that the pH of the ready-to-use composition as defined in step iii) is in the range of 8 to 11, more preferably in the range of 8.5 to 10.5.

The second aqueous composition of step iii) may be the same second composition as laid out for the two-part composition above.

It is further preferred from the viewpoint of dyeing intensity and dyeing method economy that the leave-on time as defined in step iv) is in the range of 2 min to 45 min, more preferably in the range of 5 min to 40 min, further more preferably in the range of 10 min to 30 min.

TABLE 1

| | Ingredients | Inv. Ex. 1 | Inv. Ex. 2 | Inv. Ex. 3 | Compar. Ex. 1 |
|---|---|---|---|---|---|
| Composition a) | HC Blue 18 | 0.135 | 0.135 | 0.135 | 0.135 |
| | HC Red 18 | 0.015 | 0.015 | 0.015 | 0.015 |
| | HC Yellow 16 | 0.25 | 0.25 | 0.1 | 0.25 |
| — | Disperse Black 9 | — | — | 0.1 | — |
| — | Acid Yellow 1 | — | — | 0.5 | — |
| b) | Tris-(hydroxymethyl)-aminomethane | 5.0 | 12.5 | 4.0 | — |
| — | 2-Aminomethyl propanol | — | — | — | 5.0 |
| — | Ammonia 25% w/w | — | — | 1.0 | — |
| | Water | | Ad 100.0 | | |
| Evaluation | | Intensity directly upon dyeing | | | |
| ΔE*$_{a,b}$ | Virgin hair | 62.00 | 61.95 | 61.96 | 59.31 |
| | Bleached hair | 67.07 | 67.22 | 67.09 | 66.23 |
| | Permed hair | 66.80 | 66.80 | 67.65 | 63.05 |
| | | Upon washing | | | |
| | Virgin hair | 53.56 | 52.62 | 56.80 | 51.86 |
| | Bleached hair | 68.00 | 66.23 | 63.51 | 61.10 |
| | Permed hair | 63.41 | 60.71 | 62.16 | 54.80 |
| | | Color loss/wash fastness | | | |
| | Virgin hair | 8.44 | 9.33 | 5.14 | 7.45 |
| | Bleached hair | −0.93 | 0.99 | 2.58 | 5.13 |
| | Permed hair | 3.39 | 7.09 | 5.49 | 8.25 |

The pH of the above compositions was 9.5 ± 0.3.

Discussion of Results

The examples of table 1 illustrated, that higher color intensities (high ΔE*$_{a}$,b values) were achieved with the inventive examples in respect to the comparative example. That observation was independent from hair type.

Inventive example 1 showed superior color intensity and wash fastness (ΔΔE*$_{a}$,b values) with respect to comparative example 1, which replaces the same amount of TRIS with AMP. This observation is also independent of hair type.

In addition, the best performance was found on bleached hair with respect to the comparative composition.

Methods

Hair Preparation

Commercially available goat hair (15 cm long, 2 g per bundle) was pre-washed and blow-dried prior to any treatment.

For hair having undergone perm treatment, a commercial perm was performed, which is available under the trade name Structure and Shine under the brand name Goldwell. The first step was the application of a reducing composition comprising thioglycolic acid, leaving it for 20 min on the hair, then rinsing it off and applying an oxidizing composition comprising hydrogen peroxide. The oxidizing composition was left for 15 min onto the hair and then the hair was shampooed and blow-dried. The hair obtained by this method was used for the dyeing experiments on permed hair.

For the hair undergone bleach treatment, a commercial bleach was performed, which is available under the trade name Oxycur Platin from Goldwell. The bleaching powder comprised persalts and was mixed with an oxidizing composition comprising hydrogen peroxide in a weight ration 1:1 prior to application onto the hair. Then to hair was applied the ready-to-use mixture and it was left for 20 min. The hair was then rinsed-off, shampooed, and blow-dried. The hair obtained by this method was used for the dyeing experiments on bleached hair.

Hair Dyeing

To prepare a ready-to-use composition, each of the compositions from above mere mixed with an acidic composition having a pH of 2.5 in a weight ratio of 1:1. 2 g of the resulting ready-to-use compositions were applied to the hair as prepared above and left for 20 min at ambient temperature. The hair was then rinsed-off with water and blow-dried.

Colormetric measurements were conducted on the hair streaks with a color-difference meter using the CIE colorimetric system (L*,a*,b*). The values are termed 'freshly dyed' for further calculation purposes.

Wash Fastness Experiments

Each hair streak was then placed in a shaking bath comprising a 1.5% by weight solution of sodium laureth sulfate at 40° C. and 100 rpm for 30 min. Then the hair streaks were rinsed-off with water and blow dried. Colormetric measurements were conducted again and the (L*,a*, b*) values were obtained. They are termed 'washed' for further calculation purposes.

$\Delta E^*_{a,b}$ Calculations

For assessing the color differences between washed and freshly colored hair, each L*, a*, and b* values of the samples were obtained.

$\Delta E^*$ was then calculated by the following equation:

$$\Delta E^*_{a,b} = \sqrt{(L_2-L_1)^2 + (a_2-a_1)^2 + (b_2-b_1)^2}$$

TABLE 2

|  | Ingredient | Inv. Ex. 4 | Inv. Ex. 5 | Comp. Ex. 2 |
|---|---|---|---|---|
|  |  | [% by weight active matter] | | |
| Composition | HC Blue 18 | 0.27 | 0.27 | 0.27 |
|  | HC Red 18 | 0.03 | 0.03 | 0.03 |
|  | HC Yellow 16 | 0.50 | 0.50 | 0.50 |
|  | Tris-(hydroxymethyl)-aminomethane | 0.96 | 0.5 | — |
|  | 2-Aminomethyl propanol | 1.0 | 1.0 | 1.0 |
|  | Ammonia | — | 1.84 | 3.84 |
|  | di-Na hydrogen phosphate | 1.0 | 1.0 | 1.0 |
|  | EDTA 4Na | 2.0 | 2.0 | 2.0 |
|  | Benzyl alcohol | 4.0 | 4.0 | 4.0 |
|  | Phenoxyethanol | 2.0 | 2.0 | 2.0 |
|  | Paraffin oil | 6.0 | 6.0 | 6.0 |
|  | Carboxyvinyl polymer | 2.0 | 2.0 | 2.0 |
|  | NaOH | q.s. ad pH 10 ± 0.3 | | |
|  | Water | Ad 100.0 | | |
| Evaluation $\Delta E^*_{a,b}$ | | Intensity directly upon dyeing | | |
|  | Bleached hair | 68.10 | 67.40 | 68.01 |
|  | | Wash fastness | | |
|  | Bleached hair | 67.48 | 67.44 | 58.53 |
|  | $\Delta\Delta E^*_{a,b}$ | 0.62 | −0.04 | 9.48 |

The composition from above were applied to keratin fibers without prior mixing and left for 30 min. After that, the composition was rinsed off, the keratin fibers were shampooed and blow-dried.

The wash fastness and color measurement methods as presented for table 1 were used for table 2.

Discussion of Results

The examples of table 2 illustrate the technical effect of low concentrations of TRIS. Color intensity is not generally increased with over the inventive examples, but durability/wash fastness is significantly different in comparison to comparative example 2.

The following examples are within the scope of the present invention.

Example 6

| | % by weight |
|---|---|
| HC Blue 18 | 0.1 |
| HC Red 18 | 0.05 |
| HC Yellow 16 | 0.08 |
| Tris-(hydroxymethyl)-aminomethane | 0.8 |
| 2-Aminomethyl propanol | 2.5 |
| Ceteareth-30 | 3.0 |
| Sodium lauryl sulfate | 1.5 |
| Cetearyl alcohol | 4.0 |
| Benzyl alcohol | 1.0 |
| Acrylates copolymer | 1.5 |
| NaOH/HCl | ad pH 9.5 |
| Water | ad 100.0 |

The invention claimed is:

1. A dyeing composition for keratin fibers, comprising:
one or more direct dyes selected from HC Blue 18, HC Red 18, HC Yellow 16, and salts thereof; and
tris-(hydroxymethyl)-aminomethane and salts thereof.

2. The composition according to claim 1, wherein a total concentration of the one or more direct dyes is in a range of 0.001% to 10% by weight, calculated to the total weight of the composition.

3. The composition according to claim 1, wherein a total concentration of the tris-(hydroxymethyl)-aminomethane is in a range of 0.1% to 40% by weight, calculated to the total weight of the composition.

4. The composition according to claim 1, wherein a weight ratio of the tris-(hydroxymethyl)-aminomethane to the one or more direct dyes is in a range of 0.1 to 200.

5. The composition according to claim 1, wherein the composition is an aqueous composition having a pH in the range of 7 to 12.

6. The composition according to claim 1, wherein the composition is a liquid composition at 25° C. and atmospheric pressure, and wherein the composition comprises one or more organic solvents and 1% by weight of water or less.

7. The composition according to claim 1, wherein the composition is a powder composition, and optionally comprises one or more pulverulent excipients.

8. The composition according to claim 1, further comprising one or more lipophilic compounds being liquid at 25° C. under atmospheric pressure.

9. The composition according to claim 1, wherein the composition is an emulsion and comprises one or more lipophilic compounds selected from fatty alcohols having an branched or linear, saturated or unsaturated carbon chain length in the range of C12 to C22, fatty acids having an branched or linear, saturated or unsaturated carbon chain length in the range of C12 to C22, ester oils, vegetable oils, silicone oil, and paraffin oils.

10. The composition according to claim 1, further comprising one or more organic solvents.

11. The composition according to claim 1, further comprising one or more alkalizing agents different from tris-(hydroxymethyl)-aminomethane.

12. The composition according to claim 1, further comprising one or more acids having at least one acidic proton with a pKa value of 4 or less.

13. A two-part dyeing composition, comprising:
the composition of claim 1; and
an aqueous composition having a pH in a range of 1 to 6 and optionally comprising one or more oxidizing agents.

14. A kit-of-parts, comprising:
a first composition comprising HC Blue 18, HC Red 18, HC Yellow 16, or salts thereof and tris-(hydroxymethyl)-aminomethane;
a second composition comprising one or more direct dyes selected from HC Yellow 1, Disperse black 9, and salts thereof; and
optionally a third aqueous composition having a pH in a range of 1 to 6 and optionally comprising one or more oxidizing agents.

15. A method for dyeing of keratin fibers, comprising:
applying the composition of claim 1 onto the keratin fibers and leaving it for a time period in a range of 1 min to 60 min; and
optionally rinsing off the composition and optionally drying the keratin fibers.

16. A method for dyeing keratin fibers, comprising:
mixing the composition of claim 1 with a second aqueous composition having a pH in a range of 1 to 6 and optionally comprising one or more oxidizing agents to yield a ready-to-use composition having a pH in a range of 7 to 12;
applying the ready-to-use composition onto the keratin fibers and leaving it for a time period in a range of 1 min to 60 min; and
rinsing-off the keratin fibers and optionally shampooing the keratin fibers.

17. The method according to claim 16, wherein the one or more oxidizing agents is hydrogen peroxide.

18. The composition according to claim 11, wherein the one or more alkalizing agents different from tris-(hydroxymethyl)-aminomethane is selected from ammonia, organic alkyls, alkanolamines, and salts thereof.

* * * * *